United States Patent [19]
Hughes

[11] Patent Number: 5,869,662
[45] Date of Patent: Feb. 9, 1999

[54] PHOTOCHROMIC BENZOPYRAN COMPOUNDS

[75] Inventor: Frank J. Hughes, Edina, Minn.

[73] Assignee: Vision-Ease Lens, Inc., Brooklyn Center, Minn.

[21] Appl. No.: 895,975

[22] Filed: Jul. 17, 1997

Related U.S. Application Data

[63] Continuation of Ser. No. 478,263, Jun. 7, 1995, abandoned.

[51] Int. Cl.⁶ .................. C07D 311/94; C07D 405/10; C07D 407/10; G02B 5/23
[52] U.S. Cl. .................. 544/149; 252/586; 544/378; 546/214; 549/383; 549/414; 549/460
[58] Field of Search .................. 549/383, 414, 549/460; 252/586; 546/214; 544/149, 378

[56] References Cited

U.S. PATENT DOCUMENTS

| | | | |
|---|---|---|---|
| 3,567,607 | 3/1971 | Saunders et al. | 204/159.2 |
| 4,882,438 | 11/1989 | Tanaka et al. | 548/407 |
| 4,931,221 | 6/1990 | Heller | 252/586 |
| 5,066,818 | 11/1991 | Gemert et al. | 549/389 |
| 5,106,998 | 4/1992 | Tanaka et al. | 549/331 |
| 5,238,981 | 8/1993 | Knowles | 524/110 |
| 5,244,602 | 9/1993 | Van Gemert | 252/589 |
| 5,274,132 | 12/1993 | VanGemert | 549/389 |
| 5,411,679 | 5/1995 | Kumar | 252/586 |

FOREIGN PATENT DOCUMENTS

WO 94/20869   9/1994   WIPO .

*Primary Examiner*—Johann Richter
*Assistant Examiner*—Taofiq A. Solola
*Attorney, Agent, or Firm*—Kinney & Lange, P.A.

[57] ABSTRACT

Benzopyran compounds represented by the formulas:

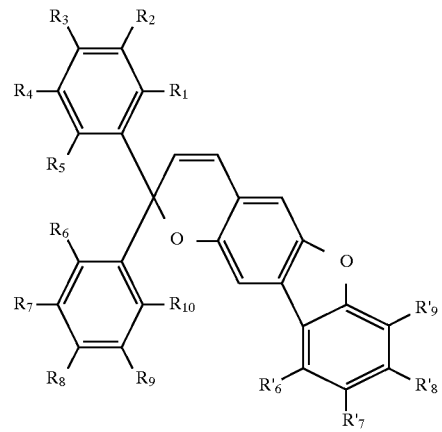

and

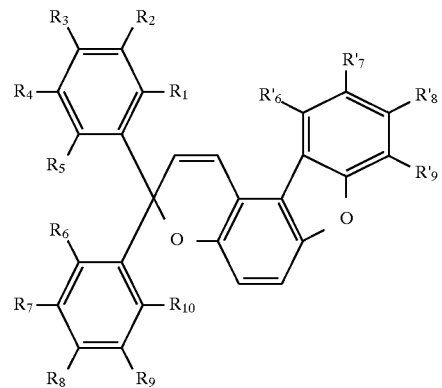

wherein $R_1$, $R_2$, $R_3$, $R_4$, $R_5$, $R_6$, $R_7$, $R_8$, $R_9$, and $R_{10}$ are selected from hydrogen, a stable organic radical, a heterocyclic group, halogen, a nitrogen-substituted group, and a nitrogen-substituted ring compound.

23 Claims, No Drawings

PHOTOCHROMIC BENZOPYRAN COMPOUNDS

This is a continuation of application Ser. No. 08/478,263, filed Jun. 7, 1995.

BACKGROUND OF THE INVENTION

The present invention generally relates to benzopyran compositions and to benzopyran compounds. More specifically, the present invention relates to photochromic benzopyran compounds and to photochromic benzopyran compositions.

Photochromism generally concerns the ability of a compound to reversibly change color under different light conditions. One particular type of photochromic phenomenon concerns the reversible change in color of a compound from an original color to a different color when the compound is exposed to a source of ultraviolet radiation, such as solar radiation or light radiated from a mercury or xenon lamp. The photochromic compound fades to the original color within a period of time after the compound is isolated from the ultraviolet radiation, such as by placing the compound in a dark room.

Various products, including optical lenses, incorporate the principal of photochromism. For example, photochromic compounds, such as naphthopyrans, are incorporated into plastic ophthalmic lenses to effect color changes in the plastic lenses when the lenses are exposed to particular lighting conditions. Additionally, different photochromic compounds may be blended to create a color effect that is different from the respective color effects of the individual photochromic compounds. As an example, a first photochromic compound that turns orange or red when activated by light and a second photochromic compound that turns blue when activated by light may be blended to form a photochromic mixture that produces a shade of gray when activated by light Several types of photochromic compounds have been reported which exhibit changes in color when exposed to ultraviolet light. One particular class of photochromic compounds includes the 3,3-disubstituted naphthopyrans. One specific group of 3,3-disubstituted naphthopyrans includes the 3H-naplitho[2,1b]pyrans. The color response of the 3H-naphtho[2,1b]pyrans to ultraviolet light extends to purple, red, orange or yellow, depending upon the composition and structure of the particular 3H-naphtho[2,1b]pyran. A general expression of the 3H-naphtho[2,1b]pyrans is provided in graphical formula I:

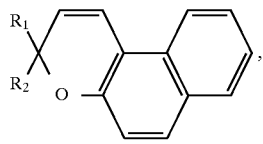

where $R_1$ and $R_2$ are substituents attached to the pyran ring at the position indicated.

Several photochromic compounds are described in U.S. Pat. No. 3,567,605 to Becker. The Becker patent describes chromenes and chromene derivatives which are photochromic at relatively low temperatures, The patent also describes chromenes and chromene derivatives which are photochromic at room temperature, such as diphenyl-3H-naphtho[2,1b]pyran, where $R_1$ and $R_2$ of formula I are each unsubstituted phenyl groups.

Additional photochromic compounds are described in U.S. Pat. No. 4,931,221 to Heller et al. One type of photochromic compound described in Heller generally has the form of graphical formula I with $R_1$ and $R_2$ being cyclopropyl radicals and with any of various substituents included on the naphtho portion of the naphthopyran rings. Heller reports a larger bathochromic shift in the visible spectrum of 3H-naphtho[2,1b]pyrans that include the cyclopropyl radicals, as compared to 3H-naphtho[2,1b]pyrans that include alkyl groups or a spirocycloalkyl group in place of the cyclopropyl radicals.

Other photochromic compounds are described in U.S. Pat. No. 5,066,818 to Gemert et al. One photochromic compound class described in Gemert generally meets graphical formula I with one of $R_1$ and $R_2$ being a substituted phenyl radical, with one of $R_1$ and $R_2$ being either a substituted or unsubstituted phenyl radical, and with various substituents included on the naphtho portion of the naphthopyran rings. Gemert lists various non-aryl groups as potential substituents of the phenyl radicals of $R_1$ and $R_2$. Gemert reports a range of decolorization rates associated with the 3H-naphtho[2,1b]pyrans that include the phenyl radicals as $R_1$ and $R_2$.

Additional photochromic compounds are described in U.S. Pat. No. 5,106,998 to Tanaka et al. Tanaka describes compounds in which $R_1$ and $R_2$ of graphical formula I are alkyl groups. Tanaka reports several fade times and maximum absorption wavelengths associated with various 3H-naphtho[2,1b]pyrans that include the alkyl radicals as $R_1$ and $R_2$ in formula I.

U.S. Pat. 5,238,981 to Knowles teaches a 3H-naphtho[2,1b]pyran compound in which $R_1$ and $R_2$ of graphical formula I are each selected from a group of organic radicals that includes phenyl and naphthyl. The organic radicals placed at $R_1$ and $R_2$ are either substituted or unsubstituted. Potential substituents of substituted organic radicals placed at $R_1$ and $R_2$, provided that one of the organic radicals placed at $R_1$ and $R_2$ is a phenyl group, include various non-aryl groups. Various potential substitutions on the naphtho portion of the naphthopyran ring are taught, including an 8-methoxy substitution. Knowles states that the number eight carbon atom substitutions, such as the 8-methoxy substitution, cause a bathochromic shift in the visible spectrum associated with activated forms of the 3H-naphtho[2,1b]pyrans and in the ultraviolet spectrum of unactivated forms of the 3H-naphtho[2,1b]pyrans.

Additional photochromic compounds are described in U.S. Pat. No. 5,244,602 to Van Gemert. Van Gemert describes 3H-naphtho[2,1b]pyrans in which $R_1$ and $R_2$ of graphical formula I are each phenyl, naphthyl, various heterocyclic groups, and certain non-aryl groups. Van Gemert also discusses substitution of various non-aryl substituents into any phenyl, naphthyl, heterocyclic, and non-aryl groups placed at $R_1$ and $R_2$. Van Gemert also states that certain substitutions at the number 5 carbon on the naphtho ring causes a bathochromic shift of the absorption maximum of the 3H-naphtho[2,1b]pyrans.

U.S. Pat. No. 5,274,132 to Van Gemert describes certain 3H-naphtho[2,1b]pyrans in which $R_1$ of graphical formula I is a phenyl group, a naphthyl group, a furyl group, or a thienyl group and in which $R_2$ of graphical formula I is an arylalkenyl radical. Van Gemert describes a bathochromic shift associated with the 3H-naphtho[2,1b]pyrans that include the arylalkenyl radical, relative to certain other naphthopyrans disclosed in U.S. Pat. No. 3,567,605.

SUMMARY OF THE INVENTION

The present invention includes benzopyran compounds represented by the formulas:

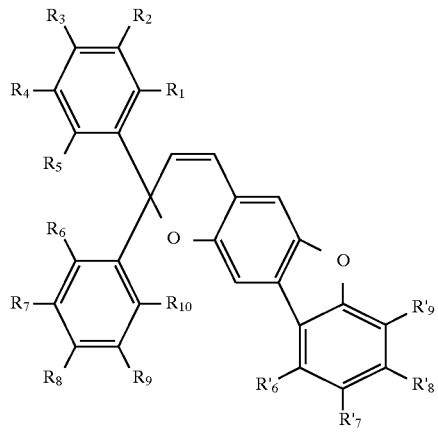

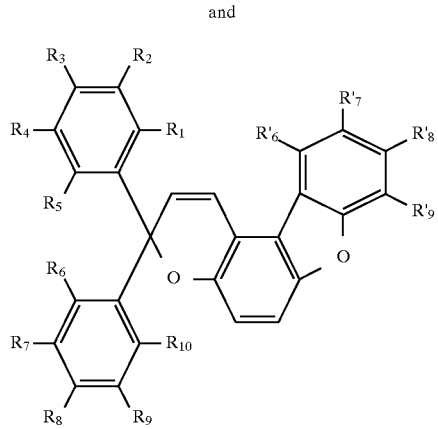

wherein $R_1$, $R_2$, $R_3$, $R_4$, $R_5$, $R_6$, $R_7$, $R_8$, $R_9$, and $R_{10}$ are selected from hydrogen, a stable organic radical, a heterocyclic group, halogen, a nitrogen-substituted group, and a nitrogen-substituted ring compound. The present invention further includes a photochromic product that includes the benzopyran compound and at least one structural isomer of the photochromic compound.

DETAILED DESCRIPTION OF THE PREFERRED EMBODIMENTS

Novel photochromic compounds have been discovered which enable high wavelength activation and deep coloring. On activation, the novel photochromic compounds produce colors that are capable of being blended with blue-producing photochromnic compounds to form photochromic blends that produce remarkably pleasing gray colors when the blends are activated by ultraviolet radiation. Furthermore, the novel photochromic compounds have acceptable fade rates and may therefore be desirably incorporated into a variety of photochromic articles.

Novel benzopyran compounds of the present invention may be represented by graphic formulas IIa and IIb as follows:

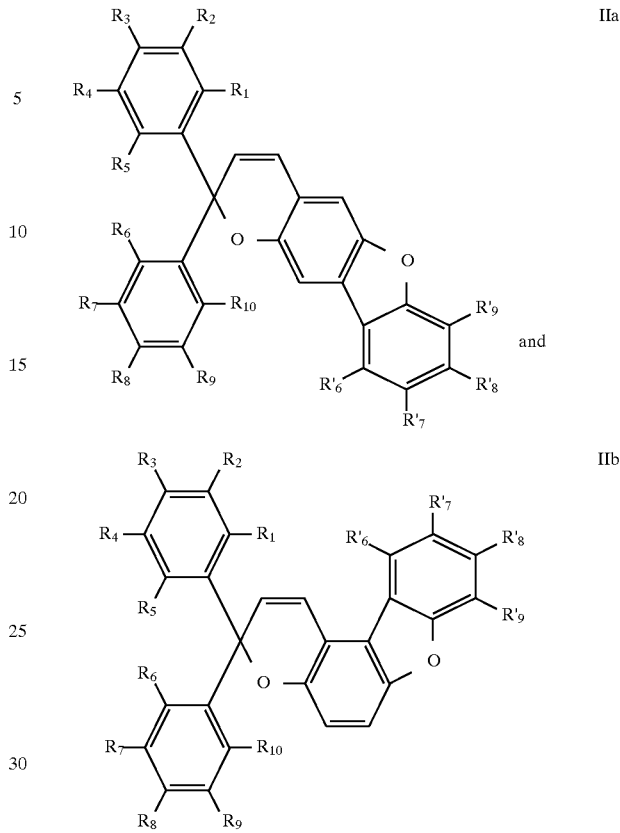

The method set forth later in this application for producing the photochromic benzopyran compounds of graphic formulas IIa and IIb forms a photochromic reaction product that includes two benzopyran compounds, namely, a structural isomer that meets graphic formula IIa and another structural isomer meeting graphic formula IIb, A variety of substituents may be placed on the pyran portion and the naphtho portion of the benzopyran rings. For example, the positions represented in graphic formulas IIa and IIb by $R_6'$, $R_7'$, $R_8'$, and $R_9'$ may each be filled with hydrogen; a stable organic radical, such as alkyl, alkoxy, unsubstituted or substituted phenyl, unsubstituted or substituted phenoxy. naphthyl naphthoxy, cycloalkyl, furyl, alkoyl, alkoyloxy, aroyl, or aroyloxy; a heterocyclic group; halogen; a nitrogen-substituted group, such as amino, dialkyl amino, or nitro; or a nitrogen-substituted ring compound, such as morpholino, piperidino, or piperazino. Also in graphic formulas IIa and IIb, $R_1$, $R_2$, $R_3$, $R_4$, $R_5$, $R_6$, $R_7$, $R_8$, $R_9$, and $R_{10}$ are each selected from the following: a stable organic radical, such as alkyl, alkoxy, unsubstituted or substituted phenyl, unsubstituted or substituted phenoxy, naphthyl, nalphthoxy, cycloalkyl, furyl, alkoyl, alkoyloxy, aroyl, or aroyloxy; a heterocyclic group; halogen; a nitrogen-substituted group, such as amino, dialkylamino, or nitro; and a nitrogen-substituted ring compound, such as morpholino, piperidino, or piperazino.

The benzopyran compounds represented by graphic formulas IIa and IIb are derivatives of 3,3-aryl-disubstituted-aryl chromenes. These benzopyran compounds exhibit a surprising and highly desirable bathochromic shift of the maximum activated wavelength. The bathochromic shift exhibited by the inventive benzopyran compounds provide photochromic species which turn orange, reddish-orange or purple when activated by a source of ultraviolet radiation. such as solar radiation or light radiated from a mercury or xenon lamp.

It has been found desirable to produce photochromic compounds with maximum activated wavelengths approaching and even exceeding 500 nanometers. Photochromic compounds with maximum activated wavelengths near or above 500 nanometers change from original states of color to deep shades of orange, reddish-orange or red when activated by ultraviolet light. The colored forms of the activated photochromic compounds fade to the original, unactivated colored states at ambient temperatures when isolated from the ultraviolet light. Photochromic compounds that turn deep shades of orange, reddish orange, or red when activated are hereinafter referred to as "intense photochromes" for purposes of this disclosure only.

The inventive benzopyrans represented by graphical formulas IIa and IIb especially the intense photochromes, exhibit a deep color and a larger bathochromic shift in the visible spectrum of the activated form, as compared to current naphthopyrans. Indeed, the inventive benzopyrans represented by graphical formulas IIa and IIb, especially the intense photochromes, approach, and in some cases exceed, a maximum activated wavelength of 500 nanometers and exhibit deep shades of orange, reddish orange, or purple when activated. One of the inventive benzopyrans represented by graphical formulas IIa and IIb surprisingly attains a maximum activated wavelength of 568 nanometers. Also, the inventive benzopyrans represented by graphical formulas IIa and IIb have acceptable fade characteristics.

One suitable method of preparing photochromic compounds having the structure of graphic formulas IIa and IIb involves reacting a suitable ketone precursor with a metal salt of an alkyne to make an intermediate. The intermediate is then reacted with either an unsubstituted fused heterocycle or a substituted fused heterocycle in the presence of a catalyst. The resultant material is then purified by recrystallization, column chromatography, or a combination of recrystallization and column chromatography.

One example of a suitable ketone precursor is 4-benzoylbiphenyl. The metal salt of the alkyne is preferably lithium acetylide and the organic solvent is preferably tetrahydrofuran. One example of the fused heterocycle is 2-hydroxy-dibenzofuran. The catalyst is preferably a catalytic amount of p-toluenesulfonic acid.

Preferred benzopyran compounds, consistent with graphic formulas IIa and IIb, include the benzopyran compounds that may be represented by graphic formulas IIIa and IIIb below:

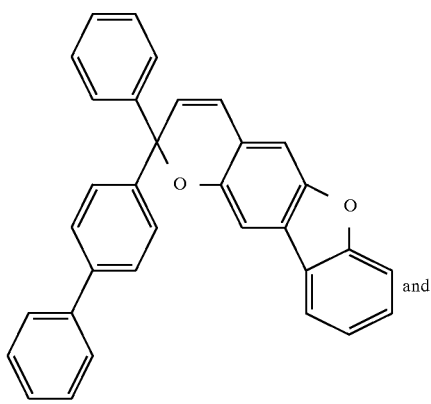

IIIa and

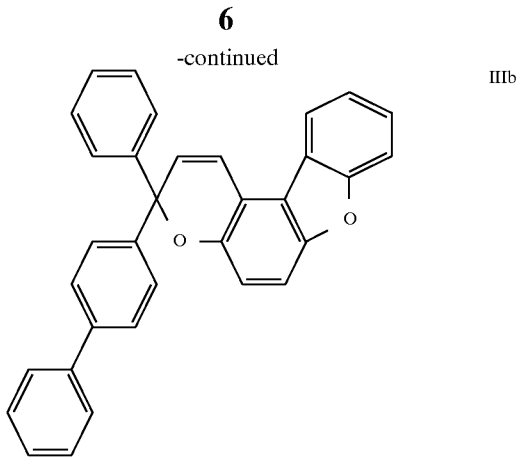

IIIb

-continued

The method set forth later in this application for producing the photochromic benzopyran compounds of graphic formulas IIIa and IIIb forms a photochromic reaction product that is believed to include both of the structural isomers that are depicted in graphic formulas IIIa and IIIb.

When dissolved in chloroform, the photochromic reaction product that includes the photochromic benzopyran compound of graphical compounds of graphic formulas IIIa and IIIb unexpectedly exhibits two maximum activated wavelengths of absorption at 456 nanometers and at 568 nanometers when irradiated with ultraviolet light. Additionally, when activated by ultraviolet light, the photochromic reaction product that includes the photochromic benzopyran compounds of graphic formulas IIIa and IIIb turns a intense shade of gray. Therefore, when a gray-turning photochromic compound is desired, the photochromic reaction product that includes the photochromic benzopyran compounds of graphic formulas IIIa and IIIb can be directly incorporated into the photochromic article without first blending the photochromic reaction product with another photochromic compound, such as a substituted spiroindolino naphthoxazine.

The intense photochromes of the present invention may be blended with one or more other photochromic compounds of different maximum activation wavelengths from that of the inventive intense photochromes to make photochromic mixtures. Preferably, the other photochromic compounds turn colors other than orange, reddish orange and purple when activated with ultraviolet light. In one embodiment, one or more of the inventive intense photochromes may be blended with another pholochromic compound which has a different maximum activation wavelength and which turns blue when activated with ultraviolet light to make the photochromic mixture. Alternatively, the photochromic reaction product that includes the photochromic benzopyran compounds of graphical formulas IIIa and IIIb may be used alone to attain the gray color upon exposure to ultraviolet light. The photochromic mixtures and the photochromic reaction product may be desirably applied to or incorporated within substrates, such as conventional synthetic plastic materials often used for optical elements.

The benzopyran compounds represented by graphic formulas IIa and IIb may be used in many applications of plastic substrates. For example, compounds represented by graphic formulas IIa and IIb may be incorporated into a host material that is applied to an article. Also, compounds represented by graphic formulas IIa and IIb may be combined with host material that is used to make the article. Additionally, compositions that contain one or more of the photochromic compounds represented by graphic formulas IIa and IIb, such as the previously mentioned photo-chromic mixtures or the photochromic reaction product, may be incorporated into the host material. The combination of the composition and host material, as already noted, may be applied to the article or may be used to make the article. Compounds represented by graphic formulas IIa and IIb and compositions containing one or more compounds represented by graphic formulas IIa and IIb may be coated onto the host material, the article, or other suitable substrate. Furthermore, the photochromic reaction product that includes the photochromic benzopyran compounds of graphic formulas IIIa and IIIb may be coated onto the host material, the article, or other suitable substrate.

Polymerized organic materials, such as synthetic polymerized plastic often used to make optical elements, are examples of the host material. Examples of the article include optical elements, such as piano and ophthalmic lenses. Non-exhaustive illustrations of suitable synthetic polymerized plastics suitable for use as the host material include polyacrylate, polycarbonate, polyvinyl alcohol, polyvinyl acetate, polyvinyl chloride, polyurethane, cellulose ester and bis-polyol (allyl carbonate) monomer-based polymer.

As used in this disclosure, including the description and the claims, the term bis-polyol (allyl carbonate) monomer and similar phrases are intended to mean and include the named monomer or prepolymer and any related monomer series contained therein. Some non-limiting examples of bis-polyol (allyl carbonate) monomers include ethylene glycol bis(allyl carbonate), di-ethylene glycol bis(2-methylallyl carbonate), diethylene glycol bis(allyl carbonate), propylene glycol bis(2-ethylallyl carbonate), 1-3-propanediol bis(allyl carbonate), 1,3-butanediol bis(allyl carbonate), 1,4-butanediol bis(2, bromoallyl carbonate), dipropylene glycol bis(allyl carbonate), trimethylene glycol bis(2-ethylallyl carbonate), pentamnethylene glycol bis(allyl carbonate), and isopropylidene bisphenol bis(allyl carbonate).

The amount of a particular one of the compounds represented by graphic formulas IIa or IIb, or a particular composition containing one of the compounds represented by graphic formulas IIIa or IIIb, that is incorporated into the host material or the coating material is defined, for purposes of this disclosure, as the photochromic amount. The photochromic amount is not critical, provided that a sufficient amount to produce a photochromic effect perceptible to the human eye is used. The photochromic amount often depends on the desired intensity of the color on activation of the particular inventive benzopyran and on the method of incorporation or application of the particular inventive benzopyran. Typically, the photochromic amount incorporated into or applied to the host material or incorporated into the coating material ranges from about 0.01 to about 20 percent by weight, based on the weight of the host material or the weight of the coating material, as applicable.

The present invention is more particularly described in the following examples which are intended as illustrations only since numerous modifications and variations within the scope of the general formulation will be apparent to those skilled in the art.

EXAMPLE 1

Step 1

Five grams of 4-benzoylbiphenyl were placed together with five grams of lithium acetylide in 250 milliliters of tetrahydrofuran and stirred for 72 hours. The resultant mixture was poured over ice and diluted with water to form an organic layer and an aqueous layer. The organic layer was separated from the aqueous layer and dried with anhydrous sodium sulfate. The dried organic layer wag evaporated to obtain a solid material. The solid material was then triturated with acetone. The triturated material was dissolved in a solvent and the solvent solution was cooled to yield a recrystallized compound. Nuclear magnetic resonance (NMR) spectroscopy showed the resultant material to be a relatively pure propargyl alcohol.

Step2

Two grams of the propargyl alcohol obtained in Step 1 were mixed with 1.25 grams of 2-hydroxydibenzofuran in 200 milliliters of benzene. Twenty milligrams of p-toluenesultonic acid were then added and the mixture was stirred under reflux for 8 hours. The resultant mixture was cooled and washed with 10% aqueous sodium hydroxide. The organic solvent (benzene) was removed using a rotary evaporator. The resulting material was dissolved in hexane and the resulting hexane solution was cooled to yield a recrystallized product. The recrystallized product was shown by nuclear magnetic resonance (NMR) spectroscopy to contain the following photochromic compounds:

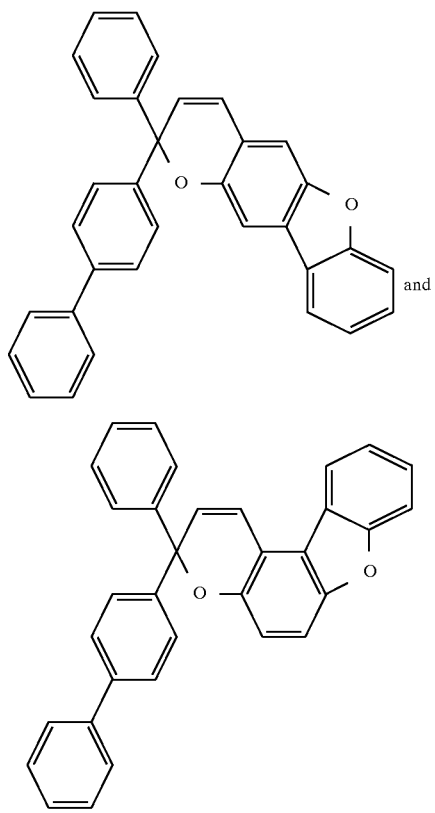

Ultraviolet visible spectroscopy indicated that the recrystallized product of Step 2, when dissolved in chloroform and irradiated with ultraviolet light of 350 nanometer wavelength, had two maximum wavelengths of absorption at 456 nanometers and at 568 nanometers.

The two maximum absorption peaks at 456 nanometers and at 568 nanometers indicate that the recrystallized product of Step 2 consists of at least two structural isomers of the photochromic compound, When the recrystallized product of Step 2 was dissolved in chloroform and subjected to thin film chromatography, one elution peak was observed for the recrystallized product. The presence of two structural isomers is supported by the thin film chromatography results, which indicate that the photochromic benzopyran compounds contained in the recrystallized product all have the same molecular weight. Thus, it is believed that the recrystallized product obtained in Step 2 contains the following photochromic compounds:

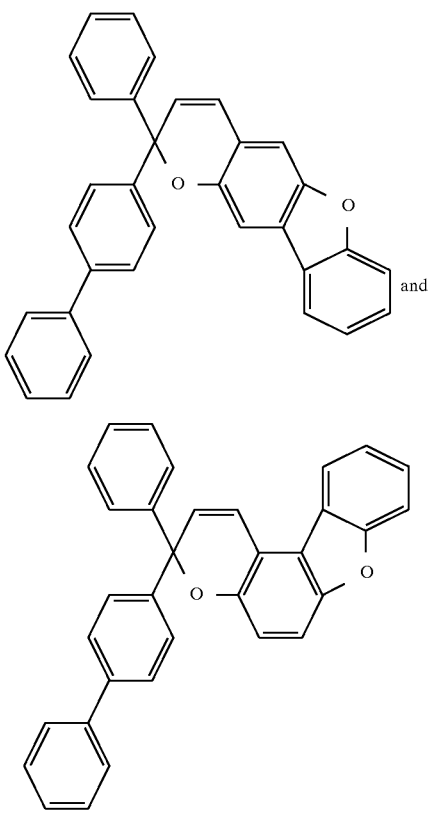

and

COMPARATIVE EXAMPLE 1

Step 1

Five grams of 4-benzoylbiphenyl were placed together with 5 grams of lithium acetylide in 250 milliliters of tetrahydrofuran and stirred for 72 hours. The resultant mixture was poured over ice and diluted with water to form an organic layer and an aqueous layer. The organic layer was separated from the aqueous layer and dried with anhydrous sodium sulfate. The dried organic material was evaporated to obtain a solid material. The solid material was triturated with acetone. Nuclear magnetic resonance (NMR) spectroscopy showed the resultant material to be relatively pure diphenyl propargyl alcohol.

Step 2

Two grams of the diphenyl propargyl alcohol obtained in Step 2 were mixed with 1.71 grams of 6-methoxy-2-naphthol in 200 milliliters of benzene. Twenty milligrams of p-toluenesulfonic acid were then added and the mixture was stirred under reflux for 8 hours. The resultant mixture was cooled and washed with 10% aqueous sodium hydroxide. The organic solvent (benzene) was removed using a rotary evaporator. The resulting material was dissolved in hexane and the resultant hexane solution was cooled to yield a recrystallized product. The recrystallized product was shown to be relatively pure 3-(4-biphenylyl)-3-phenyl-8-methoxy-3H-naphtho[2,1b]pyran by nuclear magnetic resonance NMR spectroscopy.

The recrystallized product formed in Step 2 of Example 1; the 3-(4-biphenytyl)-3-phenyl-8-methoxy-3H-naphtho[2,1b]pyran formed in Comparative Example 1; and a purchased sample of 3,3-diphenyl-3H-naphtho-[2,1b]pyran (identified as Comparative Example 2) were each individually dissolved in chloroform in separate containers. These chloroform dissolved substances were then irradiated with ultraviolet light with a maximum wavelength of 350 manometers and measured for maximum absorption wavelength, $\lambda_{max}$. The fade time, $T_{1/2}$, was then determined for each of the irradiated substances. The fade time for of the chloroform-dissolved substances is defined as the time interval, at room temperature (72° F.), for the absorbance of the activated form of each chloroform-dissolved substance to decrease to one half of the maximum absorbance, after the substance is isolated from the activating source of ultraviolet light. The maximum absorption wavelength and fade time determined for the irradiated substances of Example 1 and Comparative Examples 1-2 are presented in Table 1:

TABLE 1

| | $\lambda_{max}$ [nanometers] | $T_{1/2}$ [seconds] |
|---|---|---|
| SOLVENT | Chloroform | Chloroform |
| EXAMPLE 1 | 456, 568 | 10.2 |
| COMPARATIVE EXAMPLE | | |
| 1 | 484 | ** |
| 2 | 434 | 13 |

Comparative Example 2: Purhased 3,3-diphenyl-3H-naphtho-[2,1b]pyran
**Not Determined The values presented in Table 1 illustrate that the inventive photochromic product of Example 1 has one maximum wavelength of activation that is longer than that of the 3-(4-biphenylyl)-3-phenyl-8-methoxy-3H-naphtho[2,1b] pyran of Comparative Example 1 and the 3,3-diphenyl-3H-naphtho-[2,1b]pyran of Comparative Example 2 and also has one maximum wavelength of activation that is shorter than that of the 3-(4-biphenylyl)-3-phenyl- 8-methoxy-3H-naphtho[2,1b]pyran of Comparative Example 1. This combination of both longer and shorter maximum wavelengths of activation for the inventive photochromic product is a desirable characteristic for photochromic compositions. Additionally, the fade time, $T_{1/2}$, of the inventive photochromic product of Example 1 is 10.2 seconds, which is a desirable fade time for photochromic compositions.

Although the present invention has been described with reference to preferred embodiments, workers skilled in the art will recognize that changes may be made in form and detail without departing from the spirit and scope of the invention.

What is claimed is:

1. A benzopyran compound represented by the formula:

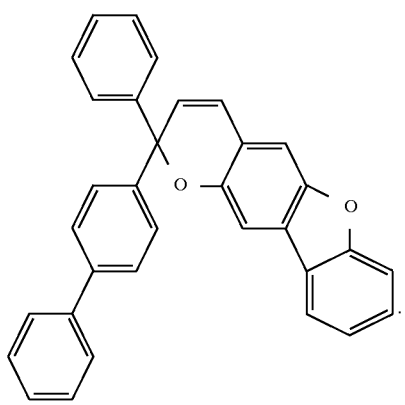

2. A benzopyran product, the benzopyran product comprising:

a benzopyran compound represented by the formula:

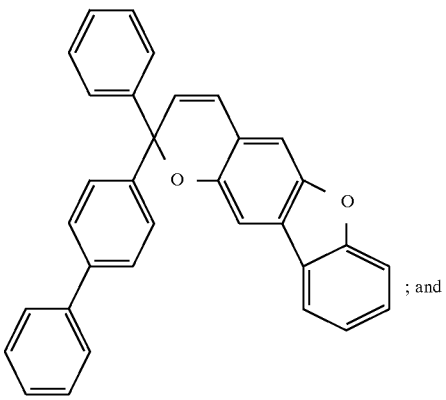

; and another benzopyran compound represented by the formula:

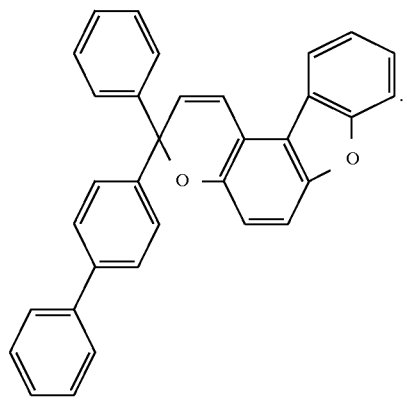

3. A benzopyran compound represented by the formula:

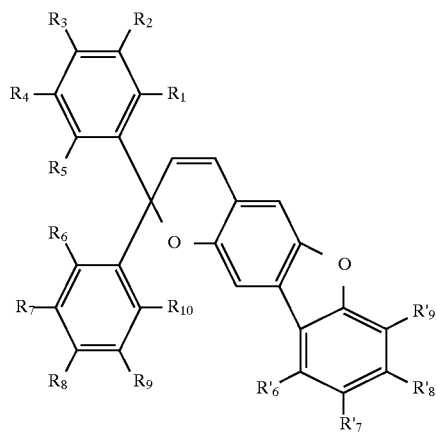

wherein $R_1$, $R_2$, $R_3$, $R_4$, $R_5$, $R_6$, $R_7$, $R_8$, $R_9$, $R_{10}$, $R_6'$, $R_7'$, $R_8'$, and $R_9'$ are each selected from the group consisting of hydrogen, alkyl, alkoxy, substituted phenyl, unsubstituted phenyl, substituted phenoxy, unsubstituted phenoxy, naphthyl, naphthoxy, cycloalkyl, furyl, alkoyl, alkoyloxy, aroyl, aroyloxy, halogen, amino, dialkyl amino, nitro, morpholino, piperidino, and piperazino, provided that:

at least one of $R_2$, $R_3$, $R_4$, $R_5$, $R_6$, $R_7$, $R_8$, and $R_9$ is selected from the group consisting of substituted phenyl, unsubstituted phenyl, substituted phenoxy, unsubstituted phenoxy, naphthyl, naphthoxy, furyl, alkoyl, alkoyloxy, aroyl, aroyloxy, amino, nitro, morpholino, piperidino, and piperazino.

4. The benzopyran compound according to claim 3 wherein $R_6'$, $R_7'$, $R_8'$, and $R_9'$ are each selected from the group consisting of hydrogen, $C_1$–$C_2$ alkyl, methoxy and ethoxy.

5. The benzopyran compound according to claim 3 wherein $R_1$, $R_2$, $R_3$, $R_4$, $R_5$, $R_6$, $R_7$, $R_8$, $R_9$, $R_{10}$, $R_6'$, $R_7'$, $R_8'$, and $R_9'$ are each selected from the group consisting of hydrogen, alkyl, alkoxy, substituted phenyl, unsubstituted phenyl, substituted phenoxy, unsubstituted phenoxy, naphthyl, naphthoxy, cycloalkyl, furyl, alkoyl, alkoyloxy, aroyl, aroyloxy, halogen, amino, dialkyl amino, nitro, morpholino, piperidino, and piperazino, provided that:

at least one of $R_2$, $R_3$, $R_4$, $R_5$, $R_6$, $R_7$, $R_8$, and $R_9$ is selected from the group consisting of substituted phenyl, unsubstituted phenyl, substituted phenoxy, unsubstituted phenoxy, furyl, alkoyl, alkoyloxy, aroyl, aroyloxy, amino, nitro, morpholino, piperidino, and piperazino.

6. The benzopyran compound according to claim 3 wherein $R_1$, $R_2$, $R_3$, $R_4$, $R_5$, $R_6$, $R_7$, $R_8$, $R_9$, $R_{10}$, $R_6'$, $R_7'$, $R_8'$, and $R_9'$ are each selected from the group consisting of hydrogen, alkyl, alkoxy, substituted phenyl, unsubstituted phenyl, substituted phenoxy, unsubstituted phenoxy, naphthyl, naphthoxy, cycloalkyl, furyl, alkoyl, alkoyloxy, aroyl, aroyloxy, halogen, amino, dialkyl amino, nitro, morpholino, piperidino, and piperazino, provided that:

at least one of $R_2$, $R_3$, $R_4$, $R_5$, $R_6$, $R_7$, $R_8$, and $R_9$ is selected from the group consisting of substituted phenyl, unsubstituted phenyl, substituted phenoxy, unsubstituted phenoxy, furyl, alkoyl, alkoyloxy, aroyl, aroyloxy, morpholino, piperidino, and piperazino.

7. The benzopyran compound according to claim 3 wherein $R_1$, $R_2$, $R_3$, $R_4$, $R_5$, $R_6$, $R_7$, $R_8$, $R_9$, $R_{10}$, $R_6'$, $R_7'$, $R_8'$, and $R_9'$ are each selected from the group consisting of hydrogen, alkyl, alkoxy, substituted phenyl, unsubstituted phenyl, substituted phenoxy, unsubstituted phenoxy, naphthyl, naphthoxy, cycloalkyl, furyl, alkoyl, alkoyloxy, aroyl, aroyloxy, halogen, amino, dialkyl amino, nitro, morpholino, piperidino, and piperazino, provided that:

at least one of $R_2$, $R_3$, $R_4$, $R_5$, $R_6$, $R_7$, $R_8$, and $R_9$ is selected from the group consisting of substituted phenyl, unsubstituted phenyl, substituted phenoxy, unsubstituted phenoxy, morpholino, piperidino, and piperazino.

8. The benzopyran compound according to claim 3 wherein $R_1$, $R_2$, $R_3$, $R_4$, $R_5$, $R_6$, $R_7$, $R_8$, $R_9$, $R_{10}$, $R_6'$, $R_7'$, $R_8'$, and $R_9'$ are each selected from the group consisting of hydrogen, alkyl, alkoxy, substituted phenyl, unsubstituted phenyl, substituted phenoxy, unsubstituted phenoxy, naphthyl, naphthoxy, cycloalkyl, furyl, alkoyl, alkoyloxy, aroyl, aroyloxy, halogen, amino, dialkyl amino, nitro, morpholino, piperidino, and piperazino, provided that:

at least one of $R_2$, $R_3$, $R_4$, $R_5$, $R_6$, $R_7$, $R_8$, and $R_9$ is selected from the group consisting of substituted phenyl, substituted phenoxy, furyl, alkoyl, alkoyloxy, aroyl, aroyloxy, amino, nitro, morpholino, piperidino, and piperazino.

9. The benzopyran compound according to claim 3 wherein $R_1$, $R_2$, $R_3$, $R_4$, $R_5$, $R_6$, $R_7$, $R_8$, $R_9$, $R_{10}$, $R_6'$, $R_7'$, $R_8'$, and $R_9'$ are each selected from the group consisting of hydrogen, alkyl, alkoxy, substituted phenyl, unsubstituted phenyl, substituted phenoxy, unsubstituted phenoxy, naphthyl, naphthoxy, cycloalkyl, furyl, alkoyl, alkoyloxy, aroyl, aroyloxy, halogen, amino, dialkyl amino, nitro, morpholino, piperidino, and piperazino, provided that:

at least one of $R_2$, $R_3$, $R_4$, $R_5$, $R_6$, $R_7$, $R_8$, and $R_9$ is selected from the group consisting of unsubstituted phenyl, unsubstituted phenoxy, furyl, alkoyl, alkoyloxy, aroyl, aroyloxy, amino, nitro, morpholino, piperidino, and piperazino.

10. The benzopyran compound according to claim 3 wherein $R_1$, $R_2$, $R_3$, $R_4$, $R_5$, $R_6$, $R_7$, $R_8$, $R_9$, $R_{10}$, $R_6'$, $R_7'$, $R_8'$, and $R_9'$ are each selected from the group consisting of hydrogen, alkyl, alkoxy, substituted phenyl, unsubstituted phenyl, substituted phenoxy, unsubstituted phenoxy, naphthyl, naphthoxy, cycloalkyl, furyl, alkoyl, alkoyloxy, aroyl, aroyloxy, halogen, amino, dialkyl amino, nitro, morpholino, piperidino, and piperazino, provided that:

at least one of $R_2$, $R_3$, $R_4$, $R_5$, $R_6$, $R_7$, $R_8$, and $R_9$ is selected from the group consisting of substituted phenyl, unsubstituted phenyl, substituted phenoxy, unsubstituted phenoxy, furyl, alkoyl, alkoyloxy, aroyl, aroyloxy, amino, and nitro.

11. The benzopyran compound according to claim 3 wherein $R_1$, $R_2$, $R_3$, $R_4$, $R_5$, $R_6$, $R_7$, $R_8$, $R_9$, $R_{10}$, $R_6'$, $R_7'$, $R_8'$, and $R_9'$ are each selected from the group consisting of hydrogen, alkyl, alkoxy, substituted phenyl, unsubstituted phenyl, substituted phenoxy, unsubstituted phenoxy, naphthyl, naphthoxy, cycloalkyl, furyl, alkoyl, alkoyloxy, aroyl, aroyloxy, halogen, amino, dialkyl amino, nitro, morpholino, piperidino, and piperazino, provided that:

at least one of $R_2$, $R_3$, $R_4$, $R_5$, $R_6$, $R_7$, $R_8$, and $R_9$ is selected from the group consisting of morpholino, piperidino, and piperazino.

12. A benzopyran product, the benzopyran product comprising:

a benzopyran compound represented by the formula:

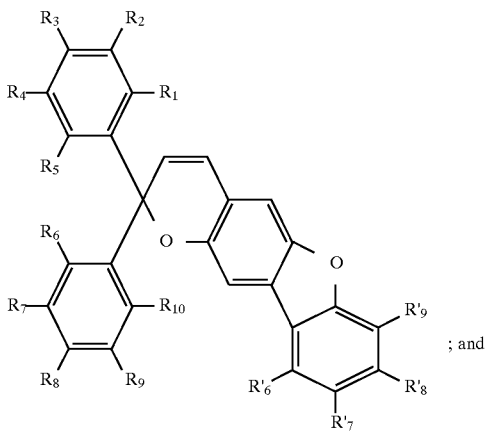

; and another benzopyran compound represented by the formula:

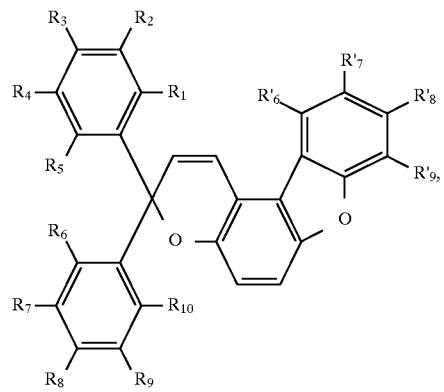

wherein $R_1$, $R_2$, $R_3$, $R_4$, $R_5$, $R_6$, $R_7$, $R_8$, $R_9$, $R_{10}$, $R_6'$, and $R_7'$, $R_8'$, $R_9'$ are each selected from the group consisting of hydrogen, alkyl, alkoxy, substituted phenyl, unsubstituted phenyl, substituted phenoxy, unsubstituted phenoxy, naphthyl, naphthoxy, cycloalkyl, furyl, alkoyl, alkoyloxy, aroyl, aroyloxy, halogen, amino, dialkyl amino, nitro, morpholino, piperidino, and piperazino, provided that:

at least one of $R_2$, $R_3$, $R_4$, $R_5$, $R_6$, $R_7$, $R_8$, and $R_9$ is selected from the group consisting of substituted phenyl, unsubstituted phenyl, substituted phenoxy, unsubstituted phenoxy, naphthyl, naphthoxy, furyl, alkoyl, alkoyloxy, aroyl, aroyloxy, amino, nitro, morpholino, piperidino, and piperazino.

13. A benzopyran compound represented by the formula:

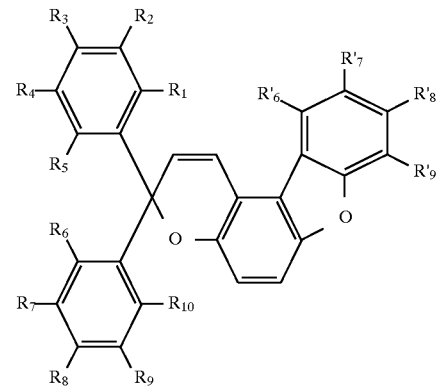

wherein $R_1$, $R_2$, $R_3$, $R_4$, $R_5$, $R_6$, $R_7$, $R_8$, $R_9$, $R_{10}$, $R_6'$, $R_7'$, $R_8'$, and $R_9'$ are each selected from the group consisting of hydrogen, alkyl, alkoxy, substituted phenyl, unsubstituted phenyl, substituted phenoxy, unsubstituted phenoxy, naphthyl, naphthoxy, cycloalkyl, furyl, alkoyl, alkoyloxy, aroyl, aroyloxy, halogen, amino, nitro, morpholino, piperidino, and piperazino, provided that:

at least one of $R_2$, $R_3$, $R_4$, $R_5$, $R_6$, $R_7$, $R_8$, and $R_9$ is selected from the group consisting of substituted phenyl, unsubstituted phenyl, substituted phenoxy, unsubstituted phenoxy, naphthyl, naphthoxy, furyl, alkoyl, alkoyloxy, aroyl, aroyloxy, amino, nitro, morpholino, piperidino, and piperazino.

14. The benzopyran compound according to claim 13 wherein $R_6'$, $R_7'$, $R_8'$, and $R_9'$ are each selected from the group consisting of hydrogen, $C_1$–$C_2$ alkyl, methoxy and ethoxy.

15. The benzopyran compound according to claim 13 wherein $R_1$, $R_2$, $R_3$, $R_4$, $R_5$, $R_6$, $R_7$, $R_8$, $R_9$, $R_{10}$, $R_6'$, $R_7'$, $R_8'$, and $R_9'$ are each selected from the group consisting of hydrogen, alkyl, alkoxy, substituted phenyl, unsubstituted phenyl, substituted phenoxy, unsubstituted phenoxy, naphthyl, naphthoxy, cycloalkyl, furyl, alkoyl, alkoyloxy, aroyl, aroyloxy, halogen, amino, dialkyl amino, nitro, morpholino, piperidino, and piperazino, provided that:
    at least one of $R_2$, $R_3$, $R_4$, $R_5$, $R_6$, $R_7$, $R_8$, and $R_9$ is selected from the group consisting of substituted phenyl, unsubstituted phenyl, substituted phenoxy, unsubstituted phenoxy, furyl, alkoyl, alkoyloxy, aroyl, aroyloxy, amino, nitro, morpholino, piperidino, and piperazino.

16. The benzopyran compound according to claim 13 wherein $R_1$, $R_2$, $R_3$, $R_4$, $R_5$, $R_6$, $R_7$, $R_8$, $R_9$, $R_{10}$, $R_6'$, $R_7'$, $R_8'$, and $R_9'$ are each selected from the group consisting of hydrogen, alkyl, alkoxy, substituted phenyl, unsubstituted phenyl, substituted phenoxy, unsubstituted phenoxy, naphthyl, naphthoxy, cycloalkyl, furyl, alkoyl, alkoyloxy, aroyl, aroyloxy, halogen, amino, dialkyl amino, nitro, morpholino, piperidino, and piperazino, provided that:
    at least one of $R_2$, $R_3$, $R_4$, $R_5$, $R_6$, $R_7$, $R_8$, and $R_9$ is selected from the group consisting of substituted phenyl, unsubstituted phenyl, substituted phenoxy, unsubstituted phenoxy, furyl, alkoyl, alkoyloxy, aroyl, aroyloxy, morpholino, piperidino, and piperazino.

17. The benzopyran compound according to claim 13 wherein $R_1$, $R_2$, $R_3$, $R_4$, $R_5$, $R_6$, $R_7$, $R_8$, $R_9$, $R_{10}$, $R_6'$, $R_7'$, $R_8'$, and $R_9'$ are each selected from the group consisting of hydrogen, alkyl, alkoxy, substituted phenyl, unsubstituted phenyl, substituted phenoxy, unsubstituted phenoxy, naphthyl, naphthoxy, cycloalkyl, furyl, alkoyl, alkoyloxy, aroyl, aroyloxy, halogen, amino, dialkyl amino, nitro, morpholino, piperidino, and piperazino, provided that:
    at least one of $R_2$, $R_3$, $R_4$, $R_5$, $R_6$, $R_7$, $R_8$, and $R_9$ is selected from the group consisting of substituted phenyl, unsubstituted phenyl, substituted phenoxy, unsubstituted phenoxy, morpholino, piperidino, and piperazino.

18. The benzopyran compound according to claim 13 wherein $R_1$, $R_2$, $R_3$, $R_4$, $R_5$, $R_6$, $R_7$, $R_8$, $R_9$, $R_{10}$, $R_6'$, $R_7'$, $R_8'$, and $R_9'$ are each selected from the group consisting of hydrogen, a alkoxy, substituted phenyl, unsubstituted phenyl, substituted phenoxy, unsubstituted phenoxy, naphthyl, naphthoxy, cycloalkyl, furyl, alkoyl, alkoyloxy, aroyl, aroyloxy, halogen, amino, dialkyl amino, nitro, morpholino, piperidino, and piperazino, provided that:
    at least one of $R_2$, $R_3$, $R_4$, $R_5$, $R_6$, $R_7$, $R_8$, and $R_9$ is selected from the group consisting of substituted phenyl, substituted phenoxy, furyl, alkoyl, alkoyloxy, aroyl, aroyloxy, amino, nitro, morpholino, piperidino, and piperazino.

19. The benzopyran compound according to claim 13 wherein $R_1$, $R_2$, $R_3$, $R_4$, $R_5$, $R_6$, $R_7$, $R_8$, $R_9$, $R_{10}$, $R_6'$, $R_7'$, $R_8'$, and $R_9'$ are each selected from the group consisting of hydrogen, alkyl, alkoxy, substituted phenyl, unsubstituted phenyl, substituted phenoxy, unsubstituted phenoxy, naphthyl, naphthoxy, cycloalkyl, furyl, alkoyl, alkoyloxy, aroyl, aroyloxy, halogen, amino, dialkyl amino, nitro, morpholino, piperidino, and piperazino, provided that:
    at least one of $R_2$, $R_3$, $R_4$, $R_5$, $R_6$, $R_7$, $R_8$, and $R_9$ is selected from the group consisting of unsubstituted phenyl, unsubstituted phenoxy, furyl, alkoyl, alkoyloxy, aroyl, aroyloxy, amino, nitro, morpholino, piperidino, and piperazino.

20. The benzopyran compound according to claim 13 wherein $R_1$, $R_2$, $R_3$, $R_4$, $R_5$, $R_6$, $R_7$, $R_8$, $R_9$, $R_{10}$, $R_6'$, $R_7'$, $R_8'$, and $R_9'$ are each selected from the group consisting of hydrogen, alky alkoxy, substituted phenyl, unsubstituted phenyl, substituted phenoxy, unsubstituted phenoxy, naphthyl, naphthoxy, cycloalkyl, furyl, alkoyl, alkoyloxy, aroyl, aroyloxy, halogen, amino, dialkyl amino, nitro, morpholino, piperidino, and piperazino, provided that:
    at least one of $R_2$, $R_3$, $R_4$, $R_5$, $R_6$, $R_7$, $R_8$, and $R_9$ is selected from the group consisting of substituted phenyl, unsubstituted phenyl, substituted phenoxy, unsubstituted phenoxy, furyl, alkoyl, alkoyloxy, aroyl, aroyloxy, amino, and nitro.

21. The benzopyran compound according to claim 13 wherein $R_1$, $R_2$, $R_3$, $R_4$, $R_{b\ 5}$, $R_6$, $R_7$, $R_8$, $R_9$, $R_{10}$, $R_6'$, $R_7'$, $R_8'$, and $R_9'$ are each selected from the group consisting of hydrogen, alkyl, alkoxy, substituted phenyl, unsubstituted phenyl, substituted phenoxy, unsubstituted phenoxy, naphthyl, naphthoxy, cycloalkyl, furyl, alkoyl, alkoyloxy, aroyl, aroyloxy, halogen, amino, dialkyl amino, nitro, morpholino, piperidino, and piperazino, provided that:
    at least one of $R_2$, $R_3$, $R_4$, $R_5$, $R_6$, $R_7$, $R_8$, and $R_9$ is selected from the group consisting of morpholino, piperidino, and piperazino.

22. The benzopyran compound according to claim 13 wherein $R_1$, $R_2$, $R_3$, $R_4$, $R_5$, $R_6$, $R_7$, $R_8$, $R_9$, $R_{10}$, $R_6'$, $R_7'$, $R_8'$, and $R_9'$ are each selected from the group consisting of hydrogen, alkyl, alkoxy, substituted phenyl, unsubstituted phenyl, substituted phenoxy, unsubstituted phenoxy, naphthyl, naphthoxy, cycloalkyl, furyl, alkoyl, alkoyloxy, aroyl, aroyloxy, halogen, amino, dialkyl amino, nitro, morpholino, piperidino, and piperazino, provided that:
    at least one of $R_2$, $R_3$, $R_4$, $R_5$, $R_6$, $R_7$, $R_8$, and $R_9$ is selected from the group consisting of substituted phenyl, unsubstituted phenyl, substituted phenoxy, and unsubstituted phenoxy.

23. A benzopyran compound represented by the formula:

* * * * *

UNITED STATES PATENT AND TRADEMARK OFFICE
CERTIFICATE OF CORRECTION

PATENT NO. : 5,869,662
DATED : FEBRUARY 9, 1999
INVENTOR(S) : FRANK J. HUGHES

It is certified that error appears in the above-identified patent and that said Letters Patent is hereby corrected as shown below:

Col. 4, line 54, delete "nalphthoxy", insert --naphthoxy--

Col. 7, line 14, delete "piano", insert --plano--

Col. 7, line 33, delete "pentamnethylene", insert --pentamethylene--

Col. 8, line 8, delete "p-toluenesultonic", insert --p-toluenesulfonic--

Col. 14, lines 19-20, delete "and $R_7'$, $R_8'$, and $R_9'$", insert --$R_7'$, $R_8'$, and $R_9'$--

Col. 16, line 13, delete "akly", insert --alkyl,--

Col. 16, line 24, delete "$R_b5$", insert --$R_5$--

Signed and Sealed this
First Day of February, 2000

Attest:

Q. TODD DICKINSON

*Attesting Officer*     *Acting Commissioner of Patents and Trademarks*